(12) United States Patent
Hofen et al.

(10) Patent No.: US 7,049,450 B2
(45) Date of Patent: May 23, 2006

(54) PROCESS FOR THE PURIFICATION OF CRUDE PROPENE OXIDE

(75) Inventors: Willi Hofen, Rodonbach (DE); Thomas Haas, Frankfurt (DE); Wolfgang Wöll, Maintal (DE); Georg Thiele, Hanau (DE)

(73) Assignees: Degussa AG, Duesseldorf (DE); UHDE GmbH, Dortmund (DE)

( * ) Notice: Subject to any disclaimer, the term of this patent is extended or adjusted under 35 U.S.C. 154(b) by 151 days.

(21) Appl. No.: 10/723,270

(22) Filed: Nov. 26, 2003

(65) Prior Publication Data

US 2004/0106811 A1    Jun. 3, 2004

Related U.S. Application Data

(60) Provisional application No. 60/428,932, filed on Nov. 26, 2002.

(51) Int. Cl.
*C07D 301/03* (2006.01)
*C07D 301/12* (2006.01)
*B01D 3/34* (2006.01)

(52) U.S. Cl. .................... 549/524; 549/524; 549/529; 549/531; 203/57; 203/64

(58) Field of Classification Search ............... 549/524, 549/529, 531; 203/57, 64
See application file for complete search history.

(56) References Cited

U.S. PATENT DOCUMENTS 2,622,060 A * 12/1952 Robeson et al. ............... 203/37
5,116,465 A * 5/1992 Yeakey et al. ................ 203/57

FOREIGN PATENT DOCUMENTS

| EP | 0 004 019 A2 | 9/1979 |
| EP | 0 100 119 A1 | 2/1984 |
| EP | 1 009 746 | 3/1999 |

* cited by examiner

*Primary Examiner*—Cecilia J. Tsang
*Assistant Examiner*—Raymond Covington
(74) *Attorney, Agent, or Firm*—Smith, Gambrell & Russell, LLP

(57) ABSTRACT

A process for the purification of a crude propene oxide containing methanol and acetaldehyde by a continuously operated extractive distillation using an extraction solvent lowering the volatility of methanol and feeding a compound containing an unsubstituted $NH_2$ group capable of reacting with acetaldehyde to a distillation column at a point above the feeding point of the crude propene oxide to give a purified propene oxide containing less than 100 ppm methanol and less than 100 ppm acetaldehyde. There is also disclosed a process for the catalytic epoxidation of propene that includes this purification stage.

20 Claims, No Drawings

PROCESS FOR THE PURIFICATION OF CRUDE PROPENE OXIDE

CROSS-REFERENCE TO RELATED APPLICATIONS

This application claims the benefit of our copending provisional patent application No. 60/428,932 filed Nov. 26, 2002 which is relied on and incorporated herein by reference.

The present invention relates to an improved process for the purification of crude propene oxide removing methanol and acetaldehyde impurities to levels below 100 ppm in a single distillation step and to a process for the preparation of propene oxide using such a purification stage.

BACKGROUND OF THE INVENTION

From EP-A 100 119 it is known that propene can be converted by hydrogen peroxide to propene oxide if a titanium silicalite is used as catalyst. Methanol is the preferred solvent leading to high catalyst activity. Crude propene oxide obtained by this process usually contains more than 1% by weight methanol and more than 200 ppm acetaldehyde from side reactions. Depending on the reaction conditions the crude propene oxide may also contain methyl formate in amounts exceeding 200 ppm.

Most of the propene oxide is used as a starting material for polyether polyols which in turn are used to make polyurethane foams. Propene oxide for this application has to meet stringent purity requirements and the content of methanol, acetaldehyde and methyl formate has to be below 100 ppm for each component. Therefore propene oxide produced with a titanium silicalite catalyst has to be further purified and impurities of methanol, acetaldehyde and, if present, methyl formate have to be removed.

Methanol, acetaldehyde and methyl formate are difficult to remove from propene oxide by simple distillation. In mixtures containing more than 98 mol-% propene oxide these compounds show virtually the same relative volatility than propene oxide. Therefore distillative purification down to low levels of methanol, acetaldehyde and methyl formate requires columns with large numbers of separation stages operated at high reflux ratios. This leads to uneconomical investment and energy costs.

Numerous methods have been suggested to remove methanol, acetaldehyde and methyl formate from propene oxide. Extractive distillation is an established method to purify propene oxide and remove oxygenated impurities.

EP-A 1 009 746 discloses the purification of propene oxide containing methanol and acetaldehyde by extractive distillation with a polar extraction solvent having a hydroxy functionality. The process also removes part of the acetaldehyde contained in the crude propene oxide. However, as can be seen from the examples, the purified propene oxide still contains acetaldehyde and methanol in amounts exceeding 100 ppm. Therefore further purification steps are necessary to achieve the desired propene oxide purity.

EP-B 004 019 discloses an alternative to extractive distillation for the removal of carbonyl compounds from propene oxide by subjecting the crude propene oxide to a simple distillation and feeding a compound containing an unsubstituted $NH_2$ group to the distillation column at a point above the feed point of the crude propene oxide. Liquid compounds with an $NH_2$ group, such as hydrazine and hydrazine hydrate are fed as such. Solid compounds with an $NH_2$ group are fed dissolved in an inert solvent. The document also describes that a solvent contained in the crude propene oxide can be separated from propene oxide in the same distillation step. However, the document contains no information or indication that methanol can be separated from propene oxide by the disclosed process.

All the solvents disclosed in EP-B 004 019 in column 7 lines 8 to 12 are of the type that can be easily separated by simple distillation from propene oxide because of sufficient differences in volatility. From the fact, that there is only a very small difference between the volatility of methanol and propene oxide at high propene oxide concentrations, a skilled person can conclude, that the process disclosed in EP-B 004 019 comprising a simple distillation is not capable to remove methanol down to the desired level of less than 100 ppm when operated at economically viable values for the number of separation stages and reflux ratio.

EP-B 004 019 also teaches that aqueous solutions of hydrazine have certain disadvantages when used for the removal of acetaldehyde: reaction of aldehyde is slow and reaction with acetaldehyde leads to insoluble products. In the propene oxide purification process disclosed in EP-B 004 019 slow reaction of aldehydes will lead to incomplete removal of acetaldehyde and the formation of insoluble products will lead to undesired deposits in the distillation column and the bottoms reboiler.

U.S. Pat. No. 2,622,060 discloses a process for the purification of a crude propene oxide by extractive distillation using an aqueous solution of an alkaline compound, such as sodium hydroxide, as the extraction solvent. Although efficient for the removal of methyl formate by saponification the process has serious drawbacks. When operated as a batch distillation it leads to excessive loss of propene oxide by propene oxide saponification. When operated as a continuous distillation purification is inefficient with the purified propene oxide containing more than 1000 ppm acetaldehyde and methanol each and having a purity of not more than 97%. Therefore further distillation steps are necessary to purify the propene oxide.

The known methods for the purification of a crude propene oxide all have a disadvantage in that they need more than one distillation step to purify a crude propene oxide containing more than 1% by weight methanol and more than 200 ppm acetaldehyde to the desired purity of less than 100 ppm methanol and acetaldehyde each.

Therefore it is an object of the present invention to provide a process for the purification of a crude propene oxide containing more than 1% by weight methanol and more than 200 ppm acetaldehyde to give a purified propene oxide containing less than 100 ppm methanol and less than 100 ppm acetaldehyde using only one distillation step.

SUMMARY OF THE INVENTION

This object has been attained by a process for the purification of a crude propene oxide containing methanol and acetaldehyde by a continuously operated extractive distillation, comprising (i) an extraction solvent is fed to the distillation column at a point above the feeding point of the crude propene oxide in an amount effective for lowering the volatility of methanol relative to the volatility of propene oxide, (ii) a compound containing an unsubstituted $NH_2$ group and capable of reacting with acetaldehyde under the conditions of distillation to form compounds with a boiling point higher than that of propene oxide is fed to the distillation column at a point above the feeding point of the crude propene oxide or is admixed with the crude propene oxide feed to the distillation column and (iii) a purified propene oxide is withdrawn from the distillation column at a position above the feeding points of the extraction solvent and the compound containing an unsubstituted NH2 group.

In a preferred embodiment the present invention relates to a process as defined above wherein the crude propene oxide is mixed with an aqueous alkaline solution and the mixture is reacted for 1 to 200 min at a temperature from 20 to 100° C. before feeding it to the extractive distillation.

The object has furthermore been attained by a process for the catalytic epoxidation of propene in which a) in a reaction step the propene is reacted with aqueous hydrogen peroxide in methanol in the presence of a titanium silicalite catalyst, b) the product stream from the reaction step is optionally passed to a pressure release step, and c) the product stream is then separated in a pre-evaporator having less than 20 theoretical separation stages into an overhead product containing propene, propene oxide and methanol, and into a bottom product containing methanol and water, 20 to 60% of the total amount of methanol introduced with the product stream being removed with the overhead product and the residue remaining in the bottom product, d) the overhead product from step c) is at least partially condensed and optionally propene and any propane present are stripped to give a condensate containing propene oxide, more than 1% by weight methanol and more than 200 wppm acetaldehyde, e) the condensate from step d) is subjected to an extractive distillation step as defined above, whereby a bottom product containing methanol and the extraction solvent is obtained, and f) all or a part of the bottom product from step c) optionally after partially removing water is recycled to the reaction step a).

DETAILED DESCRIPTION OF THE INVENTION

The purification process according to the invention is particularly suitable for the purification of crude propene oxide containing more than 1% by weight methanol and more than 200 wppm acetaldehyde (wppm=weight parts per million). The crude propene oxide is preferably obtained by epoxidation of propene with hydrogen peroxide using a titanium containing silicalite catalyst and a methanol solvent. The purified propene oxide usually contains less than 100 wppm methanol and less than 100 wppm acetaldehyde, preferably less than 50 wppm methanol and less than 50 wppm acetaldehyde.

In the purification process the crude propene oxide is subjected to a continuously operated extractive distillation. In the extractive distillation an extraction solvent is fed to the distillation column at a point above the feeding point of the crude propene oxide. Suitable as extraction solvent are compounds or compound mixtures which lower the volatility of methanol relative to the volatility of propene oxide in mixtures comprising propene oxide, methanol and the extraction solvent. The extraction solvent preferably has a boiling point of more than 50° C. to obtain a purified propene oxide with a low content of the extraction solvent. Preferably the extraction solvent comprises a polar compound containing a hydroxy group functionality.

In a preferred embodiment of the invention the extraction solvent comprises one or a mixture of several components that occur in the manufacturing process for the crude propene oxide, either as components of the feed streams or as byproducts formed in the process. Preferably the extraction solvent is water, propylene glycol, 1-methoxy-2-propanol, 2-methoxy-1-propanol, or a mixture of two or more of these compounds. Water is particularly preferred as the extraction solvent. This embodiment of the invention has the advantage that the bottom product of the extractive distillation can be combined with one or more of the process streams obtained in the process for manufacturing the crude propene oxide for the recovery of methanol and optionally the recovery of the extraction solvent. Therefore no extra distillation column is required for the recovery of methanol and optionally the extraction solvent from the bottom product of the extractive distillation.

In the purification process of the invention an additional compound containing an unsubstituted $NH_2$ group is either fed to the distillation column at a point above the feeding point of the crude propene oxide or is admixed with the crude propene oxide feed to the distillation column. Suitable are all compounds containing an unsubstituted $NH_2$ group which are capable of reacting with acetaldehyde at the conditions of distillation to form compounds with a boiling point higher than that of propene oxide. Suitable for the inventive process are also the salts of these compounds formed with acids wherein the $NH_2$ group is protonated to an $NH_3^+$ group. Preferred are compounds wherein the unsubstituted $NH_2$ group is directly bonded to a nitrogen or oxygen atom. Examples for these preferred compounds are hydrazine, hydrazine monohydrate, methylhydrazine, N,N-dimethylhydrazine and hydroxylamine as well as salts thereof, such as hydrazine sulfate, hydrazine hydrochloride or hydroxylamine sulfate. Hydrazine is particularly preferred.

In a preferred embodiment of the invention a mixture of the extraction solvent and a compound containing an unsubstituted $NH_2$ group is fed to the distillation column. Preferably this mixture is an aqueous hydrazine solution. Particularly preferred are aqueous hydrazine solutions containing from 0.5 to 5% by weight hydrazine. Contrary to the teachings of EP-B 904 019 aqueous hydrazine solutions have been found to be surprisingly efficient. Reaction with acetaldehyde in the distillation column is fast, leading to almost complete acetaldehyde conversion and no deposits of insoluble compounds are formed in the distillation column or the distillation bottom reboiler.

The amount of the extraction solvent fed to the distillation column is preferably chosen so that the mass ratio of the extraction solvent feed relative to the amount of methanol contained in the crude propene oxide feed is in the range from 0.1 to 10. The amount of the compound containing an unsubstituted $NH_2$ group fed to the distillation column is preferably chosen so that the molar ratio of the compound containing an unsubstituted $NH_2$ group relative to the acetaldehyde contained in the crude propene oxide feed is in the range from 0.5 to 2. If a mixture of the extraction solvent and the compound containing an unsubstituted $NH_2$ group is fed to the distillation column the composition of the mixture and the amounts fed are preferably chosen so that both the preferred mass ratio of the extraction solvent to methanol as well as the preferred molar ratio of the compound containing an unsubstituted $NH_2$ group relative to acetaldehyde are met.

In the purification process of the invention the purified propene oxide is withdrawn from the distillation column at a position above the feeding points of the extraction solvent and the compound containing an unsubstituted $NH_2$ group. Preferably the purified propene oxide is withdrawn at the top of the column. In this case the reflux ratio of condensate returned to the column relative to condensate withdrawn as purified propene oxide is preferably chosen in the range from 1 to 5.

The extractive distillation is preferably operated at an absolute pressure from 1 to 5 bar, more preferably at an absolute pressure from 1.5 to 2.5 bar.

The distillation column used for the extractive distillation comprises a stripping section between the column bottoms and the feed point of the crude propene oxide, an extraction section between the feed point of the crude propene oxide and the feed point of the extraction solvent and a rectifying section between the feed point of the extraction solvent and the point where the purified propene oxide is withdrawn. Preferably a distillation column is used that has a separation efficiency of 10 to 30 theoretical stages in both the stripping section and the extraction section and a separation efficiency of 20 to 60 theoretical stages in the rectifying section. The distillation column can be a tray column containing discrete trays such as sieve trays or bubble cap trays. The distillation column can also be a packed column and both random packings as well as structured packings, such as metal gauze packings can be used. The distillation column may also combine sections with discrete trays and sections with packings. The extraction section is preferably designed with discrete trays.

In a further embodiment of the invention the crude propene oxide is mixed with an aqueous alkaline solution and reacted before feeding it to the extractive distillation. The reaction time between mixing the crude propene oxide with the aqueous alkaline solution and feeding the mixture to the extractive distillation is typically in the range from 1 to 200 minutes, preferably from 1 to 30 minutes. Reaction temperature is typically from 20 to 100° C. The aqueous alkaline solution is preferably an aqueous solution of sodium hydroxide, potassium hydroxide, or sodium carbonate. Most preferred are aqueous sodium hydroxide solutions containing from 0.1 to 2% by weight sodium hydroxide. The amount of the aqueous alkaline solution is preferably chosen so that the molar ratio of hydroxide ions introduced with the aqueous alkaline solution relative to the amount of methyl formate contained in the crude propene oxide is in the range from 1.1 to 4. The mixture of crude propene oxide with the aqueous alkaline solution is preferably reacted in a tubular reactor before feeding it to the distillation. Reacting the crude propene oxide with an aqueous alkaline solution converts methyl formate contained in the crude propene oxide by hydrolyzing it to methanol and formate. The purified propene oxide obtained with this embodiment of the invention has a reduced content of methyl formate. Preferably the amount of aqueous alkaline solution is chosen to obtain a purified propene oxide having a content of methanol of less than 50 wppm, a content of acetaldehyde of less than 50 wppm and a content of methyl formate of less than 100 wppm.

The invention is also directed towards an improved process for the catalytic epoxidation of propene with aqueous hydrogen peroxide and a titanium silicalite catalyst. The improved process integrates the extractive distillation of the invention into the workup of the reaction mixture to provide propene oxide of high purity with a minimum of separation steps and a low energy requirement.

The epoxidation of propene with hydrogen peroxide is carried out in the presence of a titanium silicalite catalyst and a methanol solvent.

Crystalline titanium silicalites, preferably of the composition $(TiO_2)_x(SiO_2)_{1-x}$ where x is from 0.001 to 0.05 and having a MFI or MEL crystalline structure, known as titanium silicalite-1 and titanium silicalite-2, are suitable as catalysts for the epoxidation process according to the invention. Such catalysts may be produced for example according to the process described in U.S. Pat. No. 4,410,501.

The methanol solvent used in the epoxidation may contain 0 to 20% by weight of water due to recycling of substances in the process.

Hydrogen peroxide is preferably used as an aqueous solution containing 10 to 90% by weight of hydrogen peroxide. A hydrogen peroxide crude product obtained from the extraction step of the anthraquinone process and containing 30 to 45% by weight of hydrogen peroxide is preferably used. Alternatively, hydrogen peroxide solutions in alcohols, preferably in methanol can be used. These alcoholic solutions can be prepared by reaction of hydrogen and oxygen in presence of a noble metal catalyst and the alcohol.

Propene may be used mixed with propane in an amount of between 0 and 50 vol. % of propane. Preferably, the propene contains between 5 and 20 vol. % of propane.

In one embodiment of the invention the titanium silicalite catalyst is suspended in the reaction mixture during the reaction. The catalyst is then used in the form of a powder or in the form of a suspendable granular material that has been produced by forming in a manner known per se, for example by spray drying or fluidised bed granulation. When using a suspended catalyst, flow mixing reactors, for example stirred tank reactors or recycle reactors, as well as non-flow mixing reactors, for example tubular flow reactors, may be used for the reaction. A cascade consisting of one to three flow mixing reactors and a non-flow mixing reactor connected downstream is preferably used.

In another embodiment of the invention the titanium silicalite catalyst is used as a fixed bed over which a mixture of the feedstock materials is passed. The catalyst is then used in the form of shaped bodies that have been produced in a manner known per se, for example by extrusion with the addition of binders. For the forming process the catalyst may contain 1 to 99% of a binder or carrier material, all binders and carrier materials being suitable that do not react with hydrogen peroxide or with the epoxide under the reaction conditions employed for the epoxidation. Extrudates with a diameter of 1 to 5 mm are preferably used as fixed bed catalysts.

When using a fixed bed catalyst, reactors with bubble column characteristics can be used, i.e. the reactor contains a continuous liquid phase and a dispersed gaseous phase flows through the reactor in up-flow mode. Alternatively, reactors with trickle bed characteristics can be used, i.e. the reactor contains a gas phase and a liquid phase flows through the reactor in down-flow mode.

In a particularly preferred embodiment of the present invention the process is conducted in a fixed bed reactor and the following flow conditions are selected to maintain the catalyst bed in a trickle bed state:

$G/\lambda < 2000$ m/h and $L\psi < 50$ m/h, wherein

G is the gaseous superficial velocity defined as the gaseous flow rate in $m^3/h$ in the continuous flow reactor divided by the cross-section of the catalyst bed in $m^2$, L is the liquid superficial velocity defined as the liquid flow rate in m³/h in the continuous flow reactor divided by the cross-section of the catalyst bed in m², $$\lambda = \left[\left(\frac{\rho_G}{\rho_W}\right)\left(\frac{\rho_L}{\rho_{Air}}\right)\right]^{1/2}$$

and $$\psi = \left(\frac{\sigma_W}{\sigma_L}\right) \cdot \left[\left(\frac{\mu_L}{\mu_W}\right)\left(\frac{\rho_W}{\rho_L}\right)^2\right]^{1/3}$$

$\rho_G$ is the density of the gaseous phase in g/cm³,
$\rho_L$ is the density of the liquid phase in g/cm³,
$\rho_W$ is the density of water in g/cm³,
$\rho_{Air}$ is the density of air in g/cm³,
$\sigma_W$ is the surface tension of water in dyn/cm,
$\sigma_L$ is the surface tension of the liquid phase in dyn/cm,
$\mu_L$ is the viscosity of the liquid phase in centipoise,
$\mu_W$ is the viscosity of water in centipoise.

The epoxidation reaction is preferably carried out at temperatures between 0 and 80° C., more preferably between 40 and 65° C. According to a most preferred embodiment of the present invention the epoxidation reaction is carried out in a fixed bed reactor equipped with cooling means and the temperature profile within the reactor is maintained such that the cooling medium temperature of the cooling means is at least 30° C. and the maximum temperature within the catalyst bed is 60° C. at the most, preferably 55° C.

The epoxidation reaction is preferably carried out at elevated pressures of 10 to 40 bar, more preferably 15 to 30 bar. Propene is used in excess and the residence time in the reactor is chosen so that a hydrogen peroxide conversion of more than 90%, preferably more than 95%, is achieved. The amount of solvent used is preferably chosen so as to achieve a ratio of 1 to 10 parts by weight of solvent to one part by weight of aqueous hydrogen peroxide solution.

In a preferred embodiment of the invention the conditions for the epoxidation reaction, that is temperature, pressure and the amounts of propene, hydrogen peroxide and solvent, are chosen to obtain a multiphase reaction mixture comprising a liquid aqueous hydrogen peroxide rich phase containing methanol and a liquid organic olefin rich phase. To ensure the formation of a second liquid organic olefin rich phase the amount of propene has to be selected in excess of the amount soluble in the aqueous phase comprising water, hydrogen peroxide and methanol at the chosen temperature and pressure. Maintaining two immiscible liquid phases during the epoxidation reaction leads to improved propene oxide selectivity.

Before the working up stage the pressure of the epoxidation reaction mixture is preferably released in a pressure release stage to the pressure employed in the working up of the propene oxide. Part of the propene dissolved in the reaction mixture and possibly propane is gassed out. The resultant gas is recompressed via a compressor to the pressure prevailing in the reactor and is returned to the reaction.

The reaction mixture is then separated in a pre-evaporator into an overhead product containing propene, possibly propane, propene oxide and methanol, and into a bottom product containing methanol, water, higher boiling point byproducts, such as for example propylene glycol, unreacted hydrogen peroxide and possibly suspended titanium silicalite catalyst. The pre-evaporator according to the invention has less than 20, preferably at most 10 theoretical separation steps and is preferably designed so that the rectification section corresponds to a single distillation stage and the remaining separation effect is achieved in the stripping section. The pre-evaporator is operated at a reflux ratio of at most 1.5 and if desired may also be operated totally without reflux. The pressure in the pre-evaporator is preferably chosen in the range from 1.5 to less than 3 bar in order to avoid decomposition of hydrogen peroxide. The pre-evaporator is operated so that between 20 and 60% of the amount of solvent fed in with the reaction mixture is removed with the overhead product and the balance remains in the bottom product. Preferably, more than 95%, more preferably, more than 98% and most preferably, more than 99% of the propene oxide fed in is contained in the overhead product, and preferably, more than 90%, more preferably, more than 97% of the water fed in is contained in the bottom product.

The product stream fed to the pre-evaporator preferably contains 0.5 to 20% by weight of propene, 0 to 4% by weight of propane, 5 to 35% by weight of propene oxide, 35 to 80% by weight of methanol, 5 to 40% by weight of water, 0.1 to 8% by weight of higher boiling point byproducts, 0.1 to 5% by weight hydrogen peroxide, 0 to 5% by weight of titanium silicalite catalyst and more than 200 wppm acetaldehyde. This product stream is preferably separated in the pre-evaporator into an overhead product containing 1 to 40% by weight of propene, 0 to 10% by weight of propane, 15 to 75% by weight of propene oxide, 20 to 85% by weight of methanol, 0 to 5% by weight of water and more than 200 wppm acetaldehyde, and into a bottom product containing 0 to 2% by weight of propene oxide, 30 to 80% by weight of methanol, 15 to 65% by weight of water, 0.1 to 10% by weight of higher boiling point byproducts, 0.1 to 5% by weight of hydrogen peroxide and 0 to 10% by weight of titanium silicalite catalyst.

The overhead product from the pre-evaporator is at least partially condensed to give a condensate containing propene oxide, more than 1% by weight methanol and more than 200 wppm acetaldehyde. Preferably the overhead product is only partially condensed and the uncondensed propene, possibly mixed with propane, is recompressed via a compressor to the pressure prevailing in the reaction part and is recycled to the reaction. The propene still dissolved in the condensate and possibly propane are preferably stripped out from the condensate in a C3 stripper. Preferably the stripped-out gas is recycled to the partial condenser.

In a most preferred embodiment the overhead product from the pre-evaporator is partially condensed in a first condenser and the gaseous effluent from the first condenser is condensed in a second condenser maintained at a temperature below the temperature of the first condenser. Preferably the temperature within the first condenser is maintained at 40 to 70° C. and the temperature within the second condenser is maintained at 20 to 35° C. By using a two step condensation the amount of valuable propene oxide that can not be recovered is considerably reduced and the energy consumption for cooling is reduced compared to a one step condensation. When applying the two step condensation the condensates of both condensers are passed to the C3 stripper to remove constituents having a boiling point that is lower than that of propene oxide, whereby the gaseous effluent from the stripper is partially condensed in the second condenser and the condensate is recycled to the C3 stripper.

The condensate, obtained by at least partially condensing the overhead product from the pre-evaporator and optionally stripping it in a C3 stripper is then subjected to an extractive distillation according to the invention as described above to give a purified propene oxide containing less than 100 wppm methanol and less than 100 wppm acetaldehyde. At the bottom of the extractive distillation column a bottom product containing methanol and the extraction solvent is obtained.

The extraction solvent is preferably selected from water, propylene glycol, 1-methoxy-2-propanol, 2-methoxy-1-propanol, or a mixture thereof Water is particularly preferred as the extraction solvent. The compound containing an unsubstituted $NH_2$ group is preferably selected from hydrazine, hydrazine monohydrate, methylhydrazine, N,N-dimethylhydrazine and hydroxylamine as well as salts thereof, such as hydrazine sulfate, hydrazine hydrochloride or hydroxylamine sulfate. Hydrazine is particularly preferred.

In a most preferred embodiment the condensate is stripped in a C3 stripper and the bottom product from the C3 stripper containing 15 to 75% by weight propene oxide, 25 to 85% by weight methanol, 0 to 8% by weight water, more than 200 wppm acetaldehyde and essentially no propene or propane is subjected to an extractive distillation according to the invention using an aqueous hydrazine solution containing from 0.5 to 5% by weight hydrazine as the extraction solvent. The purified propene oxide containing less than 100 wppm methanol and less than 100 wppm acetaldehyde is withdrawn at the top of the extractive distillation column.

At least a part and preferably all of the bottom product of the pre-evaporator comprising methanol and water is recycled to the epoxidation reaction. Preferably at least a part of the water contained in the bottom product of the pre-evaporator is removed before the recycle stream is fed to the epoxidation stage.

Preferably the bottom product of the pre-evaporator is separated by distillation into a head product comprising methanol and a bottom product comprising water, high-boiling byproducts and non-reacted hydrogen peroxide. At least a part, preferably all of the head product obtained in this distillation step is recycled back to the reaction step of propene oxidation. This distillation step is preferably conducted under pressure and the pressure is selected so that the temperature of the head product comprising methanol is higher than the bottom temperature in the pre-evaporator and the C3 stripper, respectively. In this embodiment of the invention the condensation heat of the head product in said distillation step can be used to heat the pre-evaporator and the stripper and the energy requirement of the workup procedure is considerably reduced.

In a preferred embodiment of the epoxidation process the bottom product from the pre-evaporator is combined with the bottom product from the extractive distillation and the combined streams are subjected to a catalytic hydrogenation step. At least a part and preferably all of the resulting product is recycled to the epoxidation stage. Preferably at least a part of the water contained in the hydrogenated product is removed before the recycle stream is fed to the epoxidation stage.

In a most preferred embodiment an aqueous hydrazine solution containing from 0.5 to 5% by weight hydrazine is used as the extraction solvent, the bottom product from the pre-evaporator is combined with the bottom product from the extractive distillation and the combined streams are subjected to a catalytic hydrogenation step. The hydrogenated stream is then subjected to distillation into a bottom product comprising water and high-boiling byproducts and the head product comprising methanol. The head product is recycled back to the reaction step of propene epoxidation.

The catalytic hydrogenation is preferably carried out as a heterogeneous catalytic hydrogenation at a hydrogen partial pressure of 0.5 to 30 MPa. It is particularly preferred to conduct the hydrogenation step at a temperature in the range of 80° C. and 150° C., preferably 100° C. to 180° C. and at a hydrogen partial pressure of 1 to 25 MPa.

Suitable hydrogenation catalysts are selected from supported catalysts comprising one or more of metals selected from the group consisting of Ru, Rh, Pd, Pt, Ag, Ir, Fe, Cu, Ni and Co. Alternatively Raney Nickel and Raney Cobalt both optionally being doped with one or more of the above mentioned can be used. The catalyst support is preferably selected from activated carbon and metal oxides selected from $SiO_2$, $TiO_2$, $ZrO_2$ and $Al_2O_3$, mixed oxides comprising at least two of Si, Al, Ti and Zr and mixtures thereof.

The hydrogenation can be carried out continuously or batch-wise e.g., in a suspension method or a fixed-bed method. It is especially preferred to use a trickle-bed reactor. The fixed-bed catalysts to be used therein are preferably pellets with a diameter of 0.5 to 5 mm, especially 1 to 3 mm and with a length of 1 to 10 mm. The noble-metal content is in the customary range, preferably 0.5 to 5% by weight.

In a further embodiment of the epoxidation process the bottom product from the C3 stripper is mixed with an aqueous alkaline solution and the mixture is reacted for 1–200 minutes at a temperature from 20–100° C. before being fed to the extractive distillation column. The aqueous alkaline solution is preferably an aqueous solution of sodium hydroxide containing 0.1–2 percent by weight sodium hydroxide. Preferably the amount of sodium hydroxide is chosen to give a molar ratio of sodium hydroxide relative to the amount of methyl formate contained in the C3 stripper bottoms in the range from 1.1–4.

The advantages of the present invention will be apparent in view of the following examples.

EXAMPLES

Example 1

A crude propene oxide containing 52.7% by weight propene oxide, 44.3% by weight methanol, 2.2% by weight water, 1500 wppm acetaldehyde and 430 wppm methyl formate was subjected to a continuously operated extractive distillation. The extractive distillation was performed in a column with a structured packing having a separation efficiency of 80 theoretical stages operated at an absolute pressure of 1.8 bar and a reflux ratio of 2. 1241 g/h of the crude propene oxide was fed to stage 20 (counted from the bottom). Simultaneously 207 g/h of a 1.5% by weight solution of hydrazine in water was fed onto stage 40 (counted from the bottom). At the top of the column 658 g/h of purified propene oxide was withdrawn containing 99.92% by weight propene oxide, 36 wppm methanol, 70 wppm water, less than 20 wppm acetaldehyde and 390 wppm methyl formate.

Example 2

Example 1 was repeated with the following differences: 1301 g/h of a crude propene oxide containing 51.3% by weight propene oxide, 46.1% by weight methanol, 2.0% by weight water, 1200 wppm acetaldehyde and 280 wppm methyl formate were mixed with 80 g/h 0.5% by weight aqueous sodium hydroxide and reacted for 30 min at a temperature of 60° C. in a tubular reactor before being fed to the extraction column. The aqueous hydrazine solution was fed with a reduced rate of 100 g/h. At the top of the column 666 g/h of a purified propene oxide was withdrawn containing 99.98% by weight propene oxide, 33 wppm methanol, 50 wppm water, 8 wppm acetaldehyde and 52 wppm methyl formate.

What is claimed is:

1. A process for the purification of a crude propene oxide containing methanol and acetaldehyde by a continuously operated extractive distillation in a distillation column having a feeding point for the crude propene oxide, comprising:
   a. feeding an extraction solvent to the distillation column at a point of said column above the feeding point of the crude propene oxide in an amount effective for lowering the volatility of methanol relative to the volatility of propene oxide,
   b. feeding a compound containing an unsubstituted $NH_2$ group and capable of reacting with acetaldehyde under the conditions of distillation to form compounds with a boiling point higher than that of propene oxide to the distillation column at a point above the feeding point of the crude propene oxide or admixing said compounds with the crude propene oxide feed to the distillation column and
   c. withdrawing a purified propene oxide from the distillation column at a position above feeding points of the extraction solvent and the compound containing an unsubstituted $NH_2$ group.

2. The process of claim 1, wherein the crude propene oxide contains more than 1% by weight methanol and more than 200 wppm acetaldehyde.

3. The process of claim 1, wherein the purified propene oxide contains less than 100 wppm methanol and less than 100 wppm acetaldehyde.

4. The process of claim 3, wherein the purified propene oxide contains less than 50 wppm methanol and less than 50 wppm acetaldehyde.

5. The process of claim 1, wherein said column has a top and the purified propene oxide is withdrawn at the top of the column.

6. The process of claim 1, wherein a mixture of the extraction solvent and a compound containing an unsubstituted $NH_2$ group is fed to the distillation column.

7. The process of claim 1, wherein the extraction solvent is selected from the group consisting of water, propylene glycol, 1-methoxy-2-propanol, 2-methoxy-1-propanol and mixtures thereof.

8. The process of claim 7, wherein the extraction solvent is water.

9. The process of claim 1, wherein the compound containing an unsubstituted $NH_2$ group is selected from the croup consisting of hydrazine, hydrazine monohydrate and hydrazinium salts.

10. The process of claim 6, wherein the mixture is an aqueous hydrazine solution containing from 0.5 to 5% by weight hydrazine.

11. The process of claim 1, wherein the molar ratio of the compound containing an unsubstituted $NH_2$ group relative to acetaldehyde is in the range from 0.5 to 2.

12. The process of claim 1, wherein the mass ratio of the extraction solvent feed relative to the amount of methanol contained in the crude propene oxide feed is in the range from 0.1 to 10.

13. The process of claim 1, wherein the crude propene oxide is mixed with an aqueous alkaline solution and the mixture is reacted for 1 to 200 minutes, at a temperature from 20 to 100° C. before feeding it to the extractive distillation.

14. The process of claim 13, wherein the mixture is reacted for 1 to 30 minutes.

15. The process of claim 13, wherein the aqueous alkaline solution is 0.1 to 2% by weight aqueous sodium hydroxide.

16. The process of claim 13, wherein the molar ratio of hydroxide ions introduced with the aqueous alkaline solution relative to the amount of methyl formate contained in the crude propene oxide feed is in the range from 1.1 to 4.

17. The process of claim 13, wherein the mixture is reacted in a tubular reactor.

18. The process of claim 13, wherein the purified propene oxide contains less than 50 wppm methanol, less than 50 wppm acetaldehyde and less than 100 ppm methyl formate.

19. A process for the catalytic epoxidation of propene comprising:
   a. in a reaction step reacting the propene with aqueous hydrogen peroxide in methanol in the presence of a titanium silicalite catalyst to obtain a product stream,
   b. optionally passing the product stream from the reaction step to a pressure release step, and
   c. separating the product stream in a pre-evaporator having less than 20 theoretical separation stages into an overhead product containing propene, propene oxide and methanol, and into a bottom product containing methanol and water, 20 to 60% of the total amount of methanol introduced with the product stream being removed with the overhead product and residue remaining in the bottom product,
   d. at least partially condensing the overhead product from step c and optionally stripping propene and any propane present to give a condensate containing propene oxide, more than 1% by weight methanol and more than 200 wppm acetaldehyde,
   e. subjecting the condensate from step d to an extractive distillation according to claim 1, whereby a bottom product containing methanol and the extraction solvent is obtained, and
   f. recycling all or a part of the bottom product from step c optionally after partially removing water to the reaction step a.

20. The process of claim 19, further comprising:
   combining the bottom product from step c and the bottom product from step e to obtain combined products and subjecting the combined products to a catalytic hydrogenation and recycling all or a part of the resulting product optionally after partially removing water to the reaction step a.

* * * * *